US012760344B2

(12) United States Patent
Wei et al.

(10) Patent No.: US 12,760,344 B2
(45) Date of Patent: Oct. 13, 2026

(54) RELEVANT PRODUCTS AND USE OF INORGANIC PYROPHOSPHATASE IN SYNTHESIS OF NUCLEOTIDE STRANDS

(71) Applicant: HONGENE BIOTECH PTE. LTD., Singapore (SG)

(72) Inventors: Minzhi Wei, Singapore (SG); Min Guo, Singapore (SG)

(73) Assignee: HONGENE BIOTECH PTE. LTD., Singapore (SG)

( * ) Notice: Subject to any disclaimer, the term of this patent is extended or adjusted under 35 U.S.C. 154(b) by 0 days.

(21) Appl. No.: 19/251,879

(22) Filed: Jun. 27, 2025

(65) Prior Publication Data

US 2026/0209811 A1 Jul. 23, 2026

(30) Foreign Application Priority Data

Jan. 23, 2025 (CN) ......................... 202510110950.8

(51) Int. Cl.

| | |
|---|---|
| ***C12P 19/30*** | (2006.01) |
| ***C12N 9/00*** | (2006.01) |
| ***C12N 9/14*** | (2006.01) |

(52) U.S. Cl.

CPC ................ *C12P 19/30* (2013.01); *C12N 9/14* (2013.01); *C12N 9/93* (2013.01); *C12Y 306/01001* (2013.01); *C12Y 605/01003* (2013.01)

(58) Field of Classification Search

CPC .... C12Y 306/01001; C12Y 605/01003; C12N 9/93; C12N 2310/20

See application file for complete search history.

(56) References Cited

U.S. PATENT DOCUMENTS

| | | | | |
|---|---|---|---|---|
| 2012/0172258 A1* | 7/2012 | Eshoo | .................. | B01J 19/0046 506/26 |
| 2014/0051595 A1* | 2/2014 | So | ........................ | C12Q 1/6876 435/6.12 |

FOREIGN PATENT DOCUMENTS

| | | | | |
|---|---|---|---|---|
| ES | 2675167 * | 7/2018 | ......... | C12N 15/1068 |
| WO | WO-2019117714 A1 * | 6/2019 | ........... | C12Q 1/6806 |
| WO | WO-2022192189 A1 * | 9/2022 | ............. | G16B 30/00 |

* cited by examiner

*Primary Examiner* — Jane J Zara

(74) *Attorney, Agent, or Firm* — Bayramoglu Law Offices LLC

(57) ABSTRACT

The present disclosure discloses relevant products and use of inorganic pyrophosphatase in synthesis of nucleotide strands, relating to the technical field of nucleic acid synthesis. In the present disclosure, by adding the inorganic pyrophosphatase in a synthesis process of nucleotide strands, byproducts produced during ligation reaction can be greatly reduced or eliminated, a reaction rate is accelerated, and further a conversion rate and purity of a target product are improved, thereby being beneficial to fully exerting the efficacy of the nucleotide strands of interest, and providing a new approach for large-scale synthesis of high-quality nucleotide strands.

4 Claims, 1 Drawing Sheet

Specification includes a Sequence Listing.

SEQUENCE LISTING

```
Sequence total quantity: 12
SEQ ID NO: 1           moltype = RNA  length = 14
FEATURE                Location/Qualifiers
source                 1..14
                       mol_type = other RNA
                       organism = synthetic construct
SEQUENCE: 1
tttgctcaac tgtt                                              14

SEQ ID NO: 2           moltype =   length =
SEQUENCE: 2
000

SEQ ID NO: 3           moltype = RNA  length = 11
FEATURE                Location/Qualifiers
source                 1..11
                       mol_type = other RNA
                       organism = synthetic construct
SEQUENCE: 3
cattccgaac a                                                 11

SEQ ID NO: 4           moltype = RNA  length = 10
FEATURE                Location/Qualifiers
source                 1..10
                       mol_type = other RNA
                       organism = synthetic construct
SEQUENCE: 4
gttgagcaaa                                                   10

SEQ ID NO: 5           moltype = RNA  length = 14
FEATURE                Location/Qualifiers
source                 1..14
                       mol_type = other RNA
                       organism = synthetic construct
SEQUENCE: 5
cctctcttga tatg                                              14

SEQ ID NO: 6           moltype =   length =
SEQUENCE: 6
```

-continued

```
000

SEQ ID NO: 7            moltype = RNA  length = 14
FEATURE                 Location/Qualifiers
source                  1..14
                        mol_type = other RNA
                        organism = synthetic construct
SEQUENCE: 7
tctgcagatc tcat                                                 14

SEQ ID NO: 8            moltype =   length =
SEQUENCE: 8
000

SEQ ID NO: 9            moltype =   length =
SEQUENCE: 9
000

SEQ ID NO: 10           moltype = RNA  length = 12
FEATURE                 Location/Qualifiers
source                  1..12
                        mol_type = other RNA
                        organism = synthetic construct
SEQUENCE: 10
aaagacgtag ct                                                   12

SEQ ID NO: 11           moltype = RNA  length = 13
FEATURE                 Location/Qualifiers
source                  1..13
                        mol_type = other RNA
                        organism = synthetic construct
SEQUENCE: 11
ctacgtcttt gtt                                                  13

SEQ ID NO: 12           moltype =   length =
SEQUENCE: 12
000
```

RELEVANT PRODUCTS AND USE OF INORGANIC PYROPHOSPHATASE IN SYNTHESIS OF NUCLEOTIDE STRANDS

CROSS-REFERENCE TO RELATED APPLICATION

This application is based upon and claims priority to Chinese Patent Application No. 202510110950.8, filed on Jan. 23, 2025, the entire contents of which are incorporated herein by reference.

SEQUENCE LISTING

The instant application contains a Sequence Listing which has been submitted in XML format via EFS-Web and is hereby incorporated by reference in its entirety. Said XML copy is named GBCF101-Track-One_Sequence-_Listing.xml, created on Jun. 25, 2025, and is 8,000 bytes in size.

TECHNICAL FIELD

The present disclosure relates to the technical field of nucleic acid synthesis, and more specifically to relevant products and use of inorganic pyrophosphatase in synthesis of nucleotide strands.

BACKGROUND ART

Currently, industrial synthesis of oligonucleotides primarily relies on the solid-phase synthesis method. Large-scale synthesis of oligonucleotides requires multiple accumulation cycles, and during synthesis of oligonucleotides, increased strand length decreases the yield. Moreover, the increased strand length results in a certain amount of non-target nucleotide strands contained in the synthesized product which have a length not accord with that of the nucleotide strands of interest. After the chemical synthesis thereof, more non-target nucleotide strands cannot be effectively separated or removed from the synthesized product. The presence of the non-target nucleotide strands in the synthesized product often affects function, activity, etc. of the nucleotide strands of interest, and particularly for cases where the nucleotide strands of interest are antisense strand drugs, RNAi drugs, nucleic acid aptamer drugs, sgRNA drugs, etc., the presence of the non-target nucleotide strands seriously affects the nucleotide strands of interest in exerting efficacy thereof.

For nucleotide strands with a length less than or equal to 20 mer, after chemical synthesis thereof, a proportion of nucleotide strands of interest finally in a synthesized product can be increased by a purification process (for example, ion exchange column or reverse phase column). Therefore, during oligonucleotide synthesis, long fragments of 100-200 mer are divided into short fragments, and the short fragments are ligated into long fragment using RNA ligase, thereby improving the purity of the oligonucleotide.

Existing enzymatic ligation techniques have at least following problems: for high substrate concentrations, for example, concentration of ligatable nicks exceeding 2.5 mM, reaction solution containing only RNA ligase exhibits a slow reaction rate and a low conversion rate, particularly in cases where only a certain nick or some nicks complete the reaction first, while other nicks fail to complete the ligation reaction.

In view of this, the present disclosure is specifically proposed.

SUMMARY

The present disclosure aims at providing relevant products and use of inorganic pyrophosphatase in synthesis of nucleotide strands.

The present disclosure is implemented as follows.

In the first aspect, embodiments of the present disclosure provide use of inorganic pyrophosphatase in synthesis of nucleotide strands or in preparation of a product for synthesis of nucleotide strands.

In the second aspect, embodiments of the present disclosure provide an enzymatic ligation reagent, including inorganic pyrophosphatase and nucleic acid ligase.

In the third aspect, embodiments of the present disclosure provide a reaction solution, including: a nicked double-stranded nucleic acid molecule and/or a nucleic acid substrate capable of forming the nicked double-stranded nucleic acid molecule, and the enzymatic ligation reagent according to the preceding embodiments.

In the fourth aspect, embodiments of the present disclosure provide a composition, including various components of the enzymatic ligation reagent according to the preceding embodiments or various components of the reaction solution according to the preceding embodiments.

In the fifth aspect, embodiments of the present disclosure provide a kit, including the enzymatic ligation reagent according to the preceding embodiments, the reaction solution according to the preceding embodiments or the composition according to the preceding embodiments.

In the sixth aspect, embodiments of the present disclosure provide a method for synthesizing a nucleotide strand, including: performing synthesis using the enzymatic ligation reagent according to the preceding embodiments, the reaction solution according to the preceding embodiments, the composition according to the preceding embodiments or the kit according to the preceding embodiments.

The present disclosure has the following beneficial effects.

By adding the inorganic pyrophosphatase in a synthesis process of nucleotide strands, byproducts produced during ligation reaction can be greatly reduced or eliminated, a reaction rate is accelerated, and further a conversion rate and purity of a target product are improved, thereby being beneficial to fully exerting the efficacy of the nucleotide strands of interest, and providing a new approach for high-quality large-scale synthesis of nucleotide strands.

BRIEF DESCRIPTION OF DRAWINGS

In order to more clearly illustrate technical solutions of embodiments of the present disclosure, drawings which need to be used in the embodiments will be briefly introduced below. It should be understood that the drawings merely show some embodiments of the present disclosure, and thus should not be considered as limitation to the scope, and those ordinarily skilled in the art still could obtain other relevant drawings according to the drawings, without using any inventive efforts.

DETAILED DESCRIPTION OF EMBODIMENTS

Figure 1:
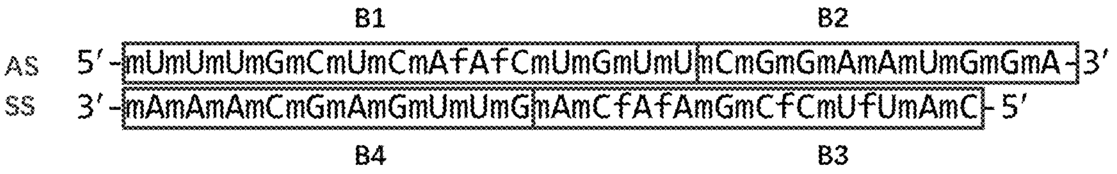
FIG. 1 shows oligonucleotides and ligation products thereof used in Example 1 of the present disclosure.

In order to make objectives, technical solutions and advantages of embodiments in the present disclosure clearer, the technical solutions in the embodiments of the present disclosure will be described clearly and completely below. Embodiments, for which no concrete conditions are specified, are carried out according to conventional conditions or conditions recommended by manufactures. Where manufacturers of reagents or instruments used are not specified, they are conventional products commercially available.

Explanation of Terms

Oligonucleotide: it generally refers to a linear polynucleotide fragment composed of 2-10 nucleotide residues linked by phosphodiester bonds. However, it should be noted that the number of nucleotides of an oligonucleotide is not strictly specified, and in some literature, polynucleotide molecules containing 30 or more, up to 200, 300, 400, or 500 nucleotide residues may also be referred to as oligonucleotides.

Natural ribonucleotide: it consists of one molecule of phosphoric acid, one molecule of ribose (a pentose sugar), and one molecule of nitrogenous base. Depending on kinds of nitrogenous bases, ribonucleotides are divided into adenine ribonucleotides, guanine ribonucleotides, cytosine ribonucleotides, and uracil ribonucleotides.

2'-deoxyribonucleotide: it consists of one molecule of phosphoric acid, one molecule of 2'-deoxyribose (deoxidation of 2' of ribose, being a hydrogen atom), and one molecule of nitrogenous base. Depending on types of nitrogenous bases, natural 2'-deoxyribonucleotides are divided into adenine deoxyribonucleotides, guanine deoxyribonucleotides, cytosine deoxyribonucleotides, and thymine deoxyribonucleotides.

Non-natural nucleotide: it refers to a nucleotide derived from modification of the phosphate group, nitrogenous base, sugar ring and glycosidic bond of a natural nucleotide.

RNA: it refers to a molecule formed by natural or non-natural ribonucleotides linked by phosphoester bonds. Although typical RNA molecules are linked together by standard phosphodiester bonds, therapeutic RNAs may contain one or more non-standard bonds. RNA may be single-stranded or double-stranded, or may include both single-stranded and double-stranded regions. In addition, ribonucleotides can also be classified into linear ribonucleotide strands and circular ribonucleotide strands according to their morphology. The circular ribonucleotide strand consists of one or more linear ribonucleotide strands linked end-to-end by phosphoester bonds, and has a closed circular structure.

DNA: it refers to a molecule composed of 2'-deoxyribonucleotides linked by phosphoester bonds.

As used herein, "wild-type" refers to a form found in nature. For example, a wild-type protein sequence refers to a form that is found in nature, and can be isolated from a source in nature and has not been intentionally modified or altered by human.

The term "nick" or "ligatable nick" herein refers to absence of a phosphodiester bond between two adjacent nucleotide fragments in a double-stranded structure. An intact phosphodiester bond may be formed by catalyzing the nick with a double-stranded ligase, that is, an intact phosphodiester bond is formed by catalyzing a 3'-hydroxyl group of one nucleotide unit at a nick and a 5'-monophosphate group of another nucleotide unit at the nick by the double-stranded ligase. "Nick" can also be understood as a notch formed in a double-stranded nucleic acid molecule due to cleavage of a phosphodiester bond.

The term "gap" herein refers to such a case that a certain strand in a double-stranded structure is broken into two strands due to deletion of one or more contiguous nucleotides, and the two strands form a gap relationship.

A nucleic acid substrate herein refers to oligonucleotides capable of forming nicked double-stranded nucleic acid molecules, where the oligonucleotides contain a monophosphate group at the 5' end and/or a hydroxyl group at the 3' end.

The term "denaturation" herein refers to a process of disrupting a hydrogen bond between base pairs of double-stranded nucleic acids such as double-stranded DNA, double-stranded RNA or DNA/RNA through high-temperature incubation, changing the double-stranded nucleic acid into single-stranded nucleic acid.

The term "annealing" herein refers to a process of gradually cooling a nucleic acid solution having undergone high-temperature denaturation to a low temperature to re-form single-stranded nucleic acid into double-stranded nucleic acid.

The term "percent sequence identity (%)" as used herein refers to comparisons among polynucleotides and polypeptides, and is determined by comparing two optimally aligned sequences over a comparison window, where a portion of a polynucleotide or polypeptide sequence in the comparison window may include additions or deletions (i.e., gaps) as compared to a reference sequence for optimal alignment of the two sequences. The percent may be calculated by determining the number of positions at which an identical nucleic acid base or amino acid residue occurs in two sequences to yield the number of matched positions, dividing the number of matched positions by the total number of positions in the comparison window, and multiplying the result by 100 to yield the percent sequence identity. Alternatively, the percent may be calculated by determining the number of positions at which either identical nucleic acid base or amino acid residue occurs in two sequences or the number of positions at which a nucleic acid base or amino acid residue is aligned with a gap to yield the number of matched positions, dividing the number of matched positions by the total number of positions in the comparison window, and multiplying the result by 100 to yield the percent sequence identity. Those skilled in the art could appreciate that there are currently many algorithms available to align sequences, such as the Smith-Waterman local homology algorithm (Smith and Waterman, Adv. Appl. Math., 2:482 [1981]), and Needleman-Wunsch global homology alignment algorithm (Needleman and Wunsch, J. Mol. Biol., 48:443 [1970]). These algorithms have been designed into relevant software by which researchers in the field can quickly align protein sequences or nucleotide sequences, such as the European Bioinformatics Institute (EMBL-EBI) open software EMBOSS Water (https://www.ebi.ac.uk/jdispatcher/psa/emboss_water) based on the Smith-Waterman algorithm and EMBOSS needle software (https://www.ebi.ac.uk/jdispatcher/psa/emboss_needle) based on the Needleman-Wunsch algorithm. Protein sequence alignment and sequence alignment identity % may be performed using the open software EMBOSS Water software. A scoring matrix employed during the alignment is BLOSUM62, with gap opening score (GAP OPEN) set to 10, and gap extension score (GAP EXTEND) set to 1.

"Reference sequence" refers to a specified sequence used as a basis for sequence comparison. The reference sequence may be a subset of a large sequence, e.g., a segment of a full-length gene or polypeptide sequence. Generally, a reference sequence is at least 20 nucleotides or amino acid residues in length, at least 25 residues in length, at least 50 residues in length, at least 100 residues in length, or a full length of a nucleic acid or polypeptide. As two polynucleotides or polypeptides may each (1) contain a sequence (i.e., a portion of a complete sequence) that is similar between two sequences, and (2) may further contain a sequence that is divergent between two sequences, sequence comparison between two (or more) polynucleotides or polypeptides is typically performed by comparing sequences of the two polynucleotides or polypeptides over the "comparison window" so as to identify and compare local regions of sequence similarity. In some embodiments, the "reference sequence" can be based on a primary amino acid sequence, where the reference sequence is a sequence that can have one or more changes in the primary sequence.

The "comparison window" refers to a conceptual segment of at least approximately 20 contiguous nucleotide positions or amino acid residues where a sequence may be compared with a reference sequence of at least 20 contiguous nucleotides or amino acids, and where the portion of the sequence in the comparison window may include additions or deletions (i.e., gaps) of 20% or less as compared to the reference sequence (which does not include additions or deletions) for optimal alignment of the two sequences. The comparison window can be longer than 20 contiguous residues, and includes, optionally 30, 40, 50, 100, or longer windows.

"Corresponding to", "reference to", or "relative to" when used in the context of the numbering of a given amino acid or polynucleotide sequence refers to the numbering of the residues of a specified reference sequence when the given amino acid or polynucleotide sequence is compared to the reference sequence. In other words, the residue number or residue position of a given polymer is designated with respect to the reference sequence rather than by the actual numerical position of the residue within the given amino acid or polynucleotide sequence. For example, a given amino acid sequence, such as that of T4 RNA ligase 2 mutant, can be aligned to a reference sequence by introducing gaps to optimize residue matches between the two sequences. In these cases, although the gaps are present, the numbering of the residue in the given amino acid or polynucleotide sequence is made with respect to the reference sequence to which it has been aligned.

The present disclosure is directed to the problems, such as production of byproducts, slow rate of enzymatic ligation reaction and low conversion rate, existing in the current synthesis process of nucleotide strands, and particularly when the concentration of ligatable nicks in a reaction solution is high (≥2.5 mM) or the amount of nucleic acid substrate in the reaction solution is ≥20 g/L, the reaction rate and conversion rate are much lower. The inventors of the present disclosure have found and validated for the first time that inorganic pyrophosphatase can effectively reduce or suppress the production of byproducts, thereby accelerating the rate of enzymatic ligation reaction, and further improving the conversion rate and purity of the nucleotide strand of interest, and especially when the concentration of ligatable nicks is relatively high (≥2.5 mM), the advantage of adding the inorganic pyrophosphatase is more remarkable.

Specific Technical Solutions

In one aspect, embodiments of the present disclosure provide use of inorganic pyrophosphatase in synthesis of nucleotide strands or in preparation of a product for synthesis of nucleotide strands.

In some embodiments, the product includes: a reagent, a kit, a chip or a combination thereof.

In another aspect, embodiments of the present disclosure provide an enzymatic ligation reagent, applied to synthesis of nucleotide strands, and including: inorganic pyrophosphatase and nucleic acid ligase.

The inorganic pyrophosphatase is derived from any of *E. coli*, yeast and thermophilic bacteria.

The inorganic pyrophosphatase may be natural pyrophosphatase, a mutant strain generated by enzyme mutation, or modification and evolution, or an enzyme capable of catalytically eliminating byproducts in an enzymatic ligation process upon enzyme fusion in the same family or with enzymes in other families.

The nucleic acid ligase catalyzes a ligatable nick of a nucleic acid substrate to form a phosphodiester bond, so as to form a target product. Adding the inorganic pyrophosphatase can significantly improve a conversion rate and purity of a synthesized target product, thereby being beneficial to fully exerting the efficacy of the target product.

In some embodiments, the nucleic acid ligase includes double-stranded ligases. The double-stranded ligase is a ligase capable of sealing a ligatable nick in a double-stranded structure. The double-stranded ligases include RNA ligases, including ligases ligating RNA duplexes and/or RNA/DNA hybrid duplexes. The inorganic pyrophosphatase is particularly suitable for synthesis of nucleotide strands employing the double-stranded ligase, provided that one of the duplex is RNA or a nick site contains RNA.

The RNA ligase undergoes three steps in enzyme ligation: in a first step, the ligase reacts with ATP to generate a ligase-AMP intermediate, releasing pyrophosphate; in a second step, the ligase-AMP intermediate binds to a nicked double-stranded substrate, transferring AMP to a 5'-phosphate terminus, and forming an adenylated nicked duplex; and in the third step, the ligase catalyzes 3'-OH of nicked RNA to attack 5'-phosphate group, forming a new 3'-5' phosphodiester bond to seal the nick and releasing AMP. The inorganic pyrophosphatase can catalytically eliminate the byproducts in the first step of reaction, so as to drive the chemical equilibrium to the right, thereby accelerating the enzymatic ligation reaction rate and further improving the conversion rate.

Specific double-stranded ligase is not particularly limited in the present disclosure, and can be selected according to actual situations, where a natural double-stranded ligase, a mutant strain generated by enzyme mutation, or modification and evolution, or an enzyme which generates a nick-sealing activity upon enzyme fusion in the same family or with enzymes in other families can be used.

In some embodiments, the double-stranded ligases include any one or more of Rnl2 family ligases and Rn15 family ligases.

In some embodiments, the double-stranded ligases include any one or more of T4 RNA ligase 2 and DraRnl (from *Naegleria gruberi*).

In some embodiments, the enzymatic ligation reagent further includes any one or more of a buffer, ATP and divalent ions.

In some embodiments, the divalent ions include any one or more of $Mg^{2+}$, $Mn^{2+}$, $Co^{2+}$ and $Zn^{2+}$.

In some embodiments, the buffer includes any one of acetate buffer, phosphate buffer, Tris buffer and HEPES buffer.

In another aspect, embodiments of the present disclosure provide a reaction solution, including: a nicked double-stranded nucleic acid molecule and/or a nucleic acid substrate capable of forming the nicked double-stranded nucleic acid molecule, and the enzymatic ligation reagent in any of the preceding embodiments.

In some embodiments, a final concentration of the inorganic pyrophosphatase in the enzymatic ligation reagent in the reaction solution ranges from 0.00001 mg/ml to 1 mg/ml, and specifically may be any one or within a range between any two of 0.00001, 0.00005, 0.0001, 0.0005, 0.001, 0.005, 0.01, 0.15, 0.2, 0.25, 0.3, 0.35, 0.4, 0.45, 0.5, 0.545, 0.6, 0.7, 0.8, 0.9 and 1 mg/ml.

In some embodiments, a final concentration of the nucleic acid ligase in the enzymatic ligation reagent in the reaction solution ranges from 0.001 mg/ml to 20 mg/ml, and specifically may be any one or within a range between any two of 0.01, 0.05, 0.1, 0.5, 1, 2, 4, 6, 7, 8, 10, 12, 14, 16, 18 and 20 mg/ml.

It should be noted that, the concentrations of the two enzymes can be adjusted according as actually required, and are not particularly limited in the present disclosure.

In some embodiments, the nicked double-stranded nucleic acid molecule includes any one or more of the following: nicked RNA duplexes and nicked RNA/DNA hybrid duplexes.

In some embodiments, in the nicked double-stranded nucleic acid molecule, the term “nicked” may mean that at least one strand of the double-stranded nucleic acid molecule has at least one nick, that is, one strand may be nicked, or both strands may be nicked.

Specifically, the nicked DNA/RNA hybrid duplexes include at least one deoxyribonucleotide, and at least one end of a nick (either the 3'-hydroxyl group and/or the 5'-phosphate group) contains RNA.

In some embodiments, the nicked double-stranded nucleic acid molecule is linear and/or circular.

In some embodiments, the nicked double-stranded nucleic acid molecule is natural and/or modified.

In some embodiments, the nicked double-stranded nucleic acid molecule includes a nucleic acid substrate or is formed by mixing or mixing and annealing a nucleic acid substrate.

In some embodiments, the nucleic acid substrate includes any one or more of the following: natural and/or modified RNA single strands, natural and/or modified RNA duplexes, natural and/or modified DNA single strands, natural and/or modified DNA/RNA hybrid single strands and natural and/or modified DNA/RNA hybrid duplexes.

In some embodiments, in the nucleic acid substrate, the RNA single strands include linear RNA single strands and/or circular RNA single strands, the RNA duplexes include linear RNA duplexes and/or circular RNA duplexes, the DNA single strands include linear DNA single strands and/or circular DNA single strands, the DNA/RNA hybrid single strands include linear DNA/RNA hybrid single strands and/or circular DNA/RNA hybrid single strands, and the DNA/RNA hybrid duplexes include linear DNA/RNA hybrid duplexes and/or circular DNA/RNA hybrid duplexes.

In some embodiments, the RNA single strands include any one or more of mRNA, antisense oligonucleotides, siRNA, sgRNA, lncRNA, CircRNA and miRNA.

When the nucleic acid substrate is double-stranded and nicked, the nucleic acid substrate itself is a nicked double-stranded nucleic acid molecule. When the nucleic acid substrate is single-stranded, the nicked double-stranded nucleic acid molecule can be formed by a step of mixing the nucleic acid substrate or mixing and then annealing the nucleic acid substrate.

In some embodiments, the nucleic acid substrate is annealed at a temperature ranging from 0° C. to 100° C., which specifically may be any one or within a range between any two of 0, 5, 10, 15, 20, 25, 30, 35, 40, 45, 50, 55, 60, 65, 70, 75, 80, 85, 90, 95, and 100° C.

In some embodiments, the process of forming the nicked double-stranded nucleic acid molecule with the nucleic acid substrate may occur in the process of mixing the nucleic acid substrate, without a separate heating and annealing process, while the nucleic acid substrate, enzyme, ATP, $Mg^{2+}$ and other essential molecules and solutions for the reaction can be directly mixed and then ligated, and the nucleic acid substrate specifically binds during the mixing, so as to form the nicked double-stranded nucleic acid molecule.

In some embodiments, the nucleic acid substrate has a fragment length of >2 nt.

In some embodiments, the fragment length of the nucleic acid substrate ranges from 2 nt to 200 nt, and specifically may be any one or within a range between any two of 2, 5, 7, 10, 13, 15, 17, 20, 23, 25, 27, 30, 33, 35, 37, 40, 43, 45, 47, 50, 53, 55, 57, 60, 63, 62, 67, 70, 73, 75, 77, 80, 85, 90, 100, 110, 120, 130, 140, 150, 160, 170, 180, 190, and 200 nt.

In some embodiments, the number of nucleic acid substrates is ≥1. For example, for circularization of circular RNA, the number of nucleic acid substrates is 1. For example, for circularization of circular RNA, the number of nucleic acid substrates is 1. The number specifically may be any one or within a range between any two of 1, 2, 4, 6, 8, 10, 12, 14, 16, 18, 20, 22, 24, 26, 28, 30, 32, 34, 36, 38, 40, 42, 44, 46, 48, and 50.

In some embodiments, the nucleic acid substrate includes a first fragment, a second fragment, a third fragment and a fourth fragment. The first fragment contains a 5'-phosphate group, the second fragment contains a 3'-hydroxyl group, and the first fragment and the second fragment can hybridize with each other and form a double-stranded structure together. The nucleic acid substrate includes the third fragment and the fourth fragment, where the third fragment contains a 3'-hydroxyl group, the fourth fragment contains a 5'-phosphate group, and the third fragment and the fourth fragment can hybridize with each other and form a double-stranded structure together. A nick is formed between the 5' end of the first fragment and the 3' end of the third fragment, the first fragment and the third fragment are ligated by a phosphodiester bond formed by a ligase between the 3' end and the 5' end, to form a nucleotide strand of interest after the ligation. A nick is formed between the 3' end of the second fragment and the 5' end of the fourth fragment, the second fragment and the fourth fragment are ligated by a phosphodiester bond formed by a ligase between the 3' end and the 5' end, to form a nucleotide strand of interest after the ligation.

In some embodiments, a molar ratio between any two nucleic acid fragments may be 0.1-1:1, and specifically may be any one or within a range between any two of 0.1:1, 0.2:1, 0.4:1, 0.6:1, 0.8:1, and 1:1.

Whether the nucleic acid substrate has a modification group is not particularly limited in the present disclosure. Compared with the scheme without addition, the scheme with inorganic pyrophosphatase has fewer by-products, faster reaction rate, and higher conversion rate and purity of the target nucleotide.

The method provided in embodiments of the present disclosure has no particular limitation on types of modifications, and all modification types are applicable.

In some embodiments, the modification includes modification for enhancing stability and/or reducing innate immune response.

In some embodiments, the modification includes any one of modification of phosphate group, modification of base, modification of sugar ring and modification of glycosidic bond.

In some embodiments, the modification of phosphate group includes any one or more of the following: 5'-(E)-vinylphosphonate modification (5'-VP), phosphorothioate modification, phosphotriester modification, 5'-methylphosphonate modification, 5'-morpholino modification, phosphorodithioate modification, methoxypropyl phosphonate modification, S-5'-C-methyl analogue modification, short-chain alkyl or cycloalkyl intersugar bond modification, short-chain heteroatom or heterocyclic intersugar bond modification, or complete substitution of phosphate group with any one of amide, aminoxy, alkoxy and triazolyl.

In some embodiments, the modification of base includes any one or more of the following: 2,4-difluorotolylribonucleoside substitution, pseudouridine modification, 2-thiouridine modification, N1-methyl pseudouridine modification, 5-methyl uridine modification, 5-methoxyuridine modification, N6-methyl adenosine modification, N6,N6-dimethyladenosine modification, 3-methyluridine modification, N7-methylguanosine modification, 2,7-dimethylguanosine modification, 2,2,7-trimethylguanosine modification, 5-methylcytidine modification, 5-hydroxymethylcytosine modification, 5-bromo-uracil modification, 5-iodo-uracil modification, propynyluracil nucleoside modification, N-ethylpiperidine-6-triazole modified adenosine modification, 6'-phenylpyrrolocytosine modification, 2-aminopurine modification, inosine modification, 2,6-diaminopurine modification, 2-pyrimidone modification and 5-methylcytosine modification.

In some embodiments, the modification of sugar ring includes any one or more of the following: 2'-methoxy modification, 2'-deoxy-2'-fluoro modification, 2'-O-methoxyethyl modification, Locked Nucleic Acid (LNA) modification, Unlocked Nucleic Acid (UNA) modification, Bridged Nucleic Acid (BNA) modification, Tricyclo-DNA (tcDNA) modification, Phosphorodiamidate Morpholino Oligomer (PMO) modification, 2'-deoxynucleotide modification, (S)-constrained ethyl bicyclic nucleic acid modification, peptide nucleic acid modification and glycomimetic modification.

In some embodiments, the glycomimetic includes any one or more of the following: cyclobutyl in cyclobutyl nucleoside for replacing pentofuranosyl group, morpholinyl in morpholino nucleic acid (MNA), peptide backbone in peptide nucleic acid (PNA), polyethylene glycol backbone in glycol nucleic acid (GNA), threitol backbone in threose nucleic acid (TNA) and butyl backbone in acyclic nucleic acid (BuNA).

In some embodiments, the modification of glycosidic bond includes, but is not limited to, replacement of C—N bond in glycosidic linkage with any one of C—C, C—O and C—S.

In some embodiments, a final concentration of the nucleic acid substrate in the reaction solution is 0.01-100 mM, and specifically may be any one or within a range between any two of 0.01, 0.05, 0.1, 0.5, 1, 5, 10, 15, 20, 25, 30, 35, 40, 45, 50, 55, 60, 65, 70, 75, 80, 85, 90, 95 and 100 mM.

In some embodiments, the final concentration of the nucleic acid substrate is 1-200 g/L, and specifically may be any one or within a range between any two of 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, and 200 g/L.

An amount of the nucleic acid substrate in the reaction solution in any of the preceding embodiments is not particularly limited, and both small and large amounts of the nucleic acid substrate are applicable to the solutions. High-concentration (>20 g/L, for example, 40 g/L, 60 g/L) substrate exhibits more significant advantages, can remarkably elevate a conversion rate of the substrate to product, and greatly reduce a content of non-target nucleotide strands in the synthesized product of nucleotide strands, so as to effectively improve the purity of the nucleotide strand of interest in the synthesized product, and further being beneficial to sufficiently exerting the effect of the target product.

The double strand of the target product includes a sense strand and an antisense strand. Typically, the sense strand undergoes an enzymatic ligation reaction first under the action of RNA ligase, followed by the other strand. During the reaction, the inorganic pyrophosphatase eliminates the byproduct pyrophosphoric acid in the reaction, and promotes the reaction to proceed towards a direction of generating the target product. The inorganic pyrophosphate has more significant effect preferably in later enzymatic ligation reaction, can promote short fragments to generate the target product more quickly, and can greatly reduce the content of the non-target nucleotide strands in the synthesized product of the nucleotide strands, so as to effectively improve the purity of the nucleotide strand of interest in the synthesized product.

In some embodiments, the nucleic acid substrate includes fragments capable of synthesizing the sense strand and acting as sense strand substrates, with the sense strand substrate being ligated by phosphodiester bonds so as to obtain the sense strand; the nucleic acid substrate includes fragments capable of synthesizing the antisense strand and acting as antisense strand substrates, with the antisense strand substrates being ligated by phosphodiester bonds so as to obtain the antisense strand. The number of sense strand substrates and antisense strand substrates is typically 1-10, and specifically may be any one or within a range between any two of 1, 2, 3, 4, 5, 6, 7, 8, 9 and 10.

The length of the nucleotide strand of interest or the target product is not particularly limited in the present disclosure. In some embodiments, the length of the nucleotide strand of interest or the target product may be ≤100 nt, 200 nt or 500 nt. In some embodiments, the length of the nucleotide strand of interest or the target product may be >10 nt, 20 nt or 50 nt.

In some embodiments, the nucleotide strand of interest may have a sequence length of 10-200 nt, which specifically may be any one or within a range between any two of 10, 20, 30, 40, 50, 60, 70, 80, 90, 100, 120, 140, 160, 180, and 200 nt.

In some embodiments, the nucleotide strand of interest is linear and/or circular.

In some embodiments, the nucleotide strand of interest is any one or more of RNA single strand, RNA duplex, DNA/RNA hybrid single strand and DNA/RNA hybrid duplex.

In some embodiments, when synthesizing the nucleotide strand using the enzymatic ligation reagent in any of the preceding embodiments or the reaction solution in any of the preceding embodiments, the conversion rate of the nucleotide strand of interest or the target product is ≥any one of 90%, 92%, 94%, 96%, 98%, and 99%.

In some embodiments, when the enzymatic ligation reagent includes ATP, a final concentration of ATP in the reaction solution ranges from 0.01 mM to 50 mM, and specifically may be any one or within a range between any two of 0.01, 0.05, 0.1, 0.5, 1, 5, 10, 20, 40, and 50 mM.

In some embodiments, when the enzymatic ligation reagent includes the divalent ions (e.g., $Mg^{2+}$), the final concentration of the divalent ions in the reaction solution ranges from 0.01 mM to 100 mM, which specifically may be any one or within a range between any two of 0.01, 0.05, 0.1, 0.5, 1, 5, 10, 20, 40, 60, 80 and 100 mM.

The buffer is not particularly limited in the present disclosure, and the buffer and pH thereof can be based on reference value of pH corresponding to optimal catalytic activity of the enzyme employed. For example, when the double-stranded ligase is T4 RNA ligase 2, the pH of the buffer may be 6.5-9.0.

In some embodiments, a concentration of the buffer is within a range of 10-1000 mM, and specifically may be any one or within a range between any two of 10, 20, 50, 100, 150, 200, 250, 300, 350, 400, 450, 500, 550, 600, 650, 700, 750, 800, 850, 900, 950, and 1000 mM, preferably 100-500 mM.

In some embodiments, the pH of the buffer is 6.5-9.0, and specifically may be any one or within a range between any two of 6.5, 6.6, 6.8, 7.0, 7.2, 7.4, 7.6, 7.8, 8.0, 8.2, 8.4, 8.6, 8.8 and 9.0.

In some embodiments, the reaction solution further includes any one or more of DTT, PEG and surfactant. PEG can be used to enhance efficiency of synthesis reaction. The surfactant can improve stability of enzyme. The surfactant includes Triton X, TWEEN, etc.

In another aspect, embodiments of the present disclosure provide a composition, including various components of the enzymatic ligation reagent according to any one of the preceding embodiments or various components of the reaction solution according to any one of the preceding embodiments.

In some embodiments, the composition further includes a termination solution. The termination solution includes EDTA. Specifically, the effect of EDTA is to terminate the synthesis reaction by chelating the divalent ions in the reaction solution. In some embodiments, the synthesis reaction of the nucleotide strands can also be terminated by heating to a denaturation temperature (e.g., 80° C.) of the nucleotide strand, without adding EDTA.

In some embodiments, a final concentration of EDTA in the reaction solution may be 0.1-100 mM, and specifically may be any one or within a range between any two of 0.1, 1, 5, 6, 7, 10, 20, 30, 40, 50, 60, 70, 80, 90, and 100 mM.

In another aspect, embodiments of the present disclosure provide a kit, including the enzymatic ligation reagent according to any one of the preceding embodiments, the reaction solution according to any one of the preceding embodiments or the composition according to any one of the preceding embodiments.

In addition, embodiments of the present disclosure provide a method for synthesizing a nucleotide strand of interest, including: performing synthesis using the enzymatic ligation reagent according to any one of the preceding embodiments, the reaction solution according to any one of the preceding embodiments, the composition according to any one of the preceding embodiments, or the kit according to any one of the preceding embodiments.

In some embodiments, synthesis conditions include: a temperature of 15-55° C. and duration of 1-48 h. The temperature specifically may be any one or within a range between any two of 15, 16, 18, 20, 22, 24, 26, 28, 30, 32, 34, 36, 37, 38, 40, 42, 44, 46, 48, 50, 52, 54, and 55° C. The duration specifically may be any one or within a range between any two of 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 18, 20, 22, 24, 26, 28, 30, 32, 34, 36, 38, 40, 42, 44, 46, and 48 h. The specific reaction temperature and reaction duration can be adjusted according to actual situations, which are not particularly limited in the present disclosure.

Characteristics and performances of the present disclosure are further described in detail below in conjunction with examples.

Example 1

1. A Reaction Solution and a Preparation Method Therefor, Specifically as Follows.

(1) Acquisition of Nucleic Acid Substrates.

4 nucleic acid fragments B1-B4 (nucleic acid substrates) listed in Table 1 were synthesized via solid-phase synthesis. The fragments were dissolved and volumetrically adjusted to obtain molar concentrations thereof. The nucleic acid substrates and ligation products thereof are as shown in FIG. 1.

TABLE 1

Non-natural Nucleic Acid Substrates

| Fragment | Name | Sequence information (5' → 3') | SEQ ID NO: |
|---|---|---|---|
| AS strand 5' end | B1 | mUmUmUmGmCmUmCmAfAfCmU mGmUmU | 1 |
| AS strand 3' end | B2 | pmCmGmGmAmAmUmGmGmA | 2 |
| SS strand 5' end | B3 | mCmAfUmUfCmCmGfAfAmCmA | 3 |
| SS strand 3' end | B4 | pmGmUmUmGmAmGmCmAmAmA | 4 |

Note: Sequences as set forth in SEQ ID NOs: 1-4 are unmodified sequences, where m represents 2'-OCH3 modification, and f represents 2'-F modification.

For convenience, oligonucleotide generated through ligation reaction of B1 and B2 is designated as sense strand (abbreviated as SS), and oligonucleotide generated from B3 and B4 is designated as antisense strand (abbreviated as AS).

(2) Preparation of Reaction Solution.

Experimental group: 20 μL of mixed solution containing the nucleic acid substrates (containing B1-B4, each fragment at concentration 2.5 mM) was placed in a 200 μL PCR tube. A buffer, $Mg^{2+}$, ATP, RNA ligase and inorganic pyrophosphatase were added, and a volume was made up to 40 μL with sterile water for injection, so as to obtain the reaction solution. See Table 2.

TABLE 2

| Components of Reaction Solution | | | |
|---|---|---|---|
| | Control Group | Experimental Group | Final concentration in reaction solution |
| Mixed solution containing the nucleic acid substrates (the nucleic acid substrates including B1-B4) | 20 μl | 20 μl | Final concentration of B1, B2, B3 and B4 being 1.25 mM, ligatable nick being 2.5 mM |
| Double-stranded ligase | 0.5 μl | 0.5 μl | 0.375 mg/ml |
| Inorganic pyrophosphatase | 0 | 0.5 μl | 0.00015 mg/ml |
| 10× reaction buffer | 4 μl | 4 μl | 1× reaction buffer |
| ATP | 1.2 μl | 1.2 μl | 2.5 mM |
| $Mg^{2+}$ | 2.8 μl | 2.8 μl | 17 mM |
| Adding to 40 μL with sterile water | 11.5 μl | 11 μl | NA |

Note: Formula of 10× reaction buffer included 500 mM Tris-Acetate, 10 mM DTT, pH=8.0; the inorganic pyrophosphatase was purchased from Hongene Biotech, Pyrophosphatase Inorganic (yeast), Cat. No. ON-025; and the double-stranded ligase was purchased from Hongene Biotech, T4 RNA Ligase 2, Cat. No. ON-544-C010.

Control group: the reaction solution was prepared through steps substantially the same as those of the experimental group, except that the inorganic pyrophosphatase was not added in the control group.

2. Synthesis of Nucleotide Strands and Analysis of Results

The reaction solutions prepared in the experimental group and the control group were respectively placed in a PCR instrument at 37° C. 1 μL was taken after 1, 4, and 16 h of the reaction, and added with 1 μL of 17 mM EDTA to be subjected to HPLC-MS detection analysis. Percentage of the target product (nucleotide strands of interest) was calculated by dividing a sum of peak areas corresponding to the AS strands and SS strands by a total peak area of nucleotides in a whole chromatogram. Experimental results of the experimental group and control group are listed in Table 3.

TABLE 3

Conversion Rates of Products in Experimental Group and Control Group after 1 h, 4 h and 16 h in Example 1

| | Conversion Rate after 1 h (%) | | | Conversion Rate after 4 h (%) | | | Conversion Rate after 16 h (%) | | |
|---|---|---|---|---|---|---|---|---|---|
| Variable | SS | AS | AS + SS | SS | AS | AS + SS | SS | AS | AS + SS |
| Experimental Group | 43.68 | 22.93 | 69.13 | 44.13 | 35.11 | 82.2 | 44.03 | 42.39 | 90.49 |
| Control Group | 34.14 | 0.99 | 36.78 | 38.96 | 6.2 | 47.06 | 43.19 | 22.86 | 68.94 |

As can be seen from the results, for the sequences in Table 1, SS strands underwent the enzymatic ligation reaction first, followed by the AS strands, and after adding the inorganic pyrophosphatase, the reaction rate of the AS strands was significantly higher than that with only the addition of RNA polymerase, demonstrating that adding the inorganic pyrophosphatase in the enzymatic ligation reaction solution can accelerate the reaction rate of the enzymatic ligation reaction, and elevate the proportion of the target product. The enhancement effect was particularly more remarkable for the AS strands, which react slowly.

Example 2

1. a Reaction Solution and a Preparation Method Thereof 3 experimental groups were provided, where Experimental Group 1 was the same as Example 1, and reaction solutions in Experimental Groups 2-3 were substantially the same as that in Example 1, except that the final concentrations of the fragments B1-B4 and ATP in the reaction solution were different, Group 1:2.5 mM ligatable nick, 20 g/L (B1-B4 total); Group 2:5 mM ligatable nick, 40 g/L; and Group 3:7.5 mM ligatable nick, 60 g/L. The concentrations of ATP in reaction systems were consistent with those of the ligatable nicks.

Experimental Groups 1-3 were respectively provided with a control group, and the inorganic pyrophosphatase was not added in the control groups.

2. Synthesis of Nucleotide Strands and Analysis of Results

The synthesis of the nucleotide strands and analysis of the results were substantially the same as those in Example 1. Reaction products after 8 h of reaction were taken and tested, with results listed below.

TABLE 4

| Conversion Rates of Products in Experimental Groups and Control Groups after 8 h in Example 2 | | | | |
|---|---|---|---|---|
| Variable | Final Concentration of Nucleic Acid Substrates in Reaction Solution | SS Product Conversion Rate (%) | AS Product Conversion Rate (%) | Product Conversion Rate (%) |
| Experimental Group | 20 g/L | 44.65 | 43.02 | 87.67 |
| | 40 g/L | 40.43 | 47.66 | 88.09 |
| | 60 g/L | 42.45 | 44.22 | 86.67 |
| Control Group | 20 g/L | 43.12 | 44.68 | 87.8 |
| | 40 g/L | 23.51 | 42.1 | 65.61 |
| | 60 g/L | 15.69 | 36.48 | 52.17 |

As can be seen from the results of the experimental groups, at the same enzyme amount, all of 20 g/L, 40 g/L and 60 g/L can achieve the conversion rate of approximately 87%. While for the control groups, the reaction concentration 20 g/L exhibited the product conversion rate of approximately 87%, and 40 g/L and 60 g/L showed significantly reduced conversion rates, particularly for the conversation rates of the SS strand product, which were remarkably lower than that at 20 g/L. Therefore, the present example demonstrates that for a high substrate concentration, for example, the ligatable nick concentration exceeding 2.5 mM, the reaction solution only containing RNA ligase exhibits slow reaction rates and low conversion rates, particularly when only a certain nick or some nicks complete the reaction prematurely, while others fail, adding the inorganic pyrophosphatase to the reaction system can enhance the reaction rate and conversion rate of the high-concentration substrates, especially when two nicks are present in the reaction, the inorganic pyrophosphatase has a notable advantage in accelerating the reaction rate of the subsequent nick.

Example 3

1. A Reaction Solution and a Preparation Method Therefor 7 experimental groups were provided, with substantially the same reaction solution as that in Example 1, except that: (1) the nucleic acid substrates were different; and (2) the final concentrations of the nucleic acid substrates and ATP in the reaction solutions were different.

(1) Nucleic Acid Substrate

Figure 2:
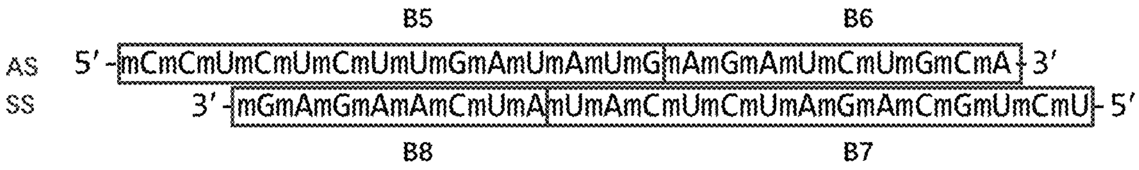
FIG. 2 shows oligonucleotides and ligation products thereof used in Example 3 of the present disclosure.

See FIG. 2 for information of the nucleic acid substrates and ligation products thereof.

TABLE 5

| Non-natural Nucleic Acid Substrates | | | |
|---|---|---|---|
| Fragment | Name | Sequence Information (5' → 3') | SEQ. ID.NO |
| AS strand 5' end | B5 | mCmCmUmCmUmCmUmUmGmA mUmAmUmG | 5 |
| AS strand 3' end | B6 | pmAmGmAmUmCmUmGmCmA | 6 |
| SS strand 5' end | B7 | mUmCmUmGmCmAmGmAmUmC mUmCmAmU | 7 |
| SS strand 3' end | B8 | pmAmUmCmAmAmGmAmG | 8 |

Note: Sequences as set forth in SEQ ID NOs: 5-8 are unmodified sequences, where m represents 2'-OCH3 modification, and f represents 2'-F modification. SEQ ID NOs: 5-8 in the sequence listing are unmodified sequences.

For convenience, oligonucleotide generated through ligation reaction of B5 and B6 is designated as sense strand (abbreviated as SS), and oligonucleotide generated from B7 and B8 is designated as antisense strand (abbreviated as AS).

(2) Final Concentrations of the Nucleic Acid Substrates in the Reaction Solutions.

Experimental Group 1:1.88 mM ligatable nick, 15 g/L (B5-B8 total); Experimental Group 2:3.76 mM ligatable nick, 30 g/L; Experimental Group 3:5.64 mM ligatable nick, 45 g/L; Experimental Group 4:7.52 mM ligatable nick, 60 g/L; Experimental Group 5:8.46 mM ligatable nick, 67.5 g/L; Experimental Group 6:9.4 mM ligatable nick, 75 g/L; and Experimental and Group 7:10.16 mM ligatable nick, 81 g/L. The concentrations of ATP in reaction systems were consistent with those of the ligatable nicks.

Experimental Groups 1-7 were respectively provided with a control group, and the inorganic pyrophosphatase was not added in the control groups.

2. Synthesis of Nucleotide Strands and Analysis of Results

The synthesis of the nucleotide strands and analysis of the results were substantially the same as those in Example 1. Reaction products after 4 h and 16 h of reaction were taken and detected, with results listed below.

TABLE 6

| Conversion Rates of Products in Experimental Groups and Control Groups after 4 h and 16 h in Example 3 | | | | | | | |
|---|---|---|---|---|---|---|---|
| | Final Concentration of Nucleic Acid | 4 h | | | 16 h | | |
| Variable | Substrates in Reaction Solution | SS Product Conversion Rate (%) | AS Product Conversion Rate (%) | Product Conversion Rate (%) | SS Product Conversion Rate (%) | AS Product Conversion Rate (%) | Product Conversion Rate (%) |
| Experimental Group | 15 g/L | 41.45 | 47.93 | 89.38 | 41.86 | 48.1 | 89.96 |
| | 30 g/L | 41.88 | 47.98 | 89.86 | 42.47 | 48.24 | 90.71 |
| | 45 g/L | 41.1 | 47.14 | 88.24 | 42.29 | 47.42 | 89.71 |
| | 60 g/L | 36.08 | 41.52 | 77.6 | 42.19 | 48.03 | 90.22 |
| | 67.5 g/L | 32.03 | 29.94 | 61.97 | 41.83 | 47.74 | 89.57 |
| | 75 g/L | 29.55 | 25.28 | 54.83 | 41.38 | 48.27 | 89.65 |
| | 81 g/L | 28.36 | 18.86 | 47.22 | 42.41 | 49.23 | 91.64 |
| Control Group | 15 g/L | 42.21 | 46.88 | 89.09 | 43.36 | 47.31 | 90.67 |
| | 30 g/L | 40.52 | 38.24 | 78.76 | 42.6 | 45.32 | 87.92 |
| | 45 g/L | 34.67 | 30.14 | 64.81 | 40.98 | 41.67 | 82.65 |
| | 60 g/L | 32.44 | 25.19 | 57.63 | 38.66 | 38.61 | 77.27 |

TABLE 6-continued

Conversion Rates of Products in Experimental Groups and Control Groups after 4 h and 16 h in Example 3

| Variable | Final Concentration of Nucleic Acid Substrates in Reaction Solution | 4 h SS Product Conversion Rate (%) | 4 h AS Product Conversion Rate (%) | 4 h Product Conversion Rate (%) | 16 h SS Product Conversion Rate (%) | 16 h AS Product Conversion Rate (%) | 16 h Product Conversion Rate (%) |
|---|---|---|---|---|---|---|---|
| | 67.5 g/L | 32.72 | 19.13 | 51.85 | 37.02 | 32.8 | 69.82 |
| | 75 g/L | 28.22 | 17.48 | 45.7 | 33.5 | 30.62 | 64.12 |
| | 81 g/L | 27.21 | 10.46 | 37.67 | 33.13 | 19.85 | 52.98 |

As can be seen from the results of the experimental groups, at the same enzyme amount, all of 15 g/L-81 g/L can achieve the conversion rate of approximately 90%. While for the control groups, the reaction concentrations 15 g/L-45 g/L exhibited the conversion rates of approximately 85%, and 60 g/L-81 g/L showed significantly reduced conversion rates, particularly for the conversation rates of the SS strand product, which were lower than those at 15 g/L-45 g/L. Therefore, the present example demonstrates that for a high substrate concentration, for example, the ligatable nick concentration exceeding 3.76 mM, the reaction solution only containing RNA ligase exhibits slow reaction rates and low conversion rates, particularly when only a certain nick or some nicks complete the reaction prematurely, while others fail, adding the inorganic pyrophosphatase to the reaction system can enhance the reaction rate and conversion rate of the high-concentration substrates, especially when two nicks are present in the reaction, the inorganic pyrophosphatase has a notable advantage in accelerating the reaction rate of the subsequent nick.

Example 4

1. a Reaction Solution and a Preparation Method Thereof, Specifically as Follows.

4 experimental groups were provided, with substantially the same reaction solution as that in Example 1, except that: (1) the nucleic acid substrates were different; and (2) the final concentrations of the nucleic acid substrates and ATP in the reaction solutions were different.

(1) Acquisition of Nucleic Acid Substrates.

4 nucleic acid fragments B9-B12 (nucleic acid substrates) listed in Table 7 were synthesized via solid-phase synthesis. The fragments were dissolved and volumetrically adjusted to obtain molar concentrations thereof.

Figure 3:
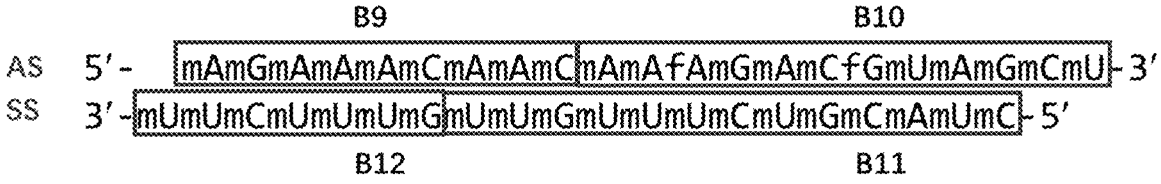
FIG. 3 shows oligonucleotides and ligation products thereof used in Example 4 of the present disclosure.

The nucleic acid substrates and ligation products thereof are as shown in FIG. 3.

TABLE 7

Non-natural Nucleic Acid Substrates

| Fragment | Name | Sequence Information (5' → 3') | SEQ. ID.NO |
|---|---|---|---|
| AS strand 5' end | B9 | mAmGmAmAmAmCmAmAmC | 9 |
| AS strand 3' end | B10 | pmAmAfAmGmAmCfGmUm AmGmCmU | 10 |
| SS strand 5' end | B11 | mCmUmAmCmGmUmCmUm UmUmGmUmU | 11 |
| SS strand 3' end | B12 | pmGmUmUmUmCmUmU | 12 |

Note: Sequences as set forth in SEQ ID NOs: 9-12 are unmodified sequences, where m represents 2'-OCH3 modification, and f represents 2'-F modification. SEQ ID NOs: 9-12 in the sequence listing are unmodified sequences.

For convenience, oligonucleotide generated through ligation reaction of B9 and B10 is designated as sense strand (abbreviated as SS), and oligonucleotide generated from B11 and B12 is designated as antisense strand (abbreviated as AS).

(2) Final Concentrations of the Nucleic Acid Substrates in the Reaction Solutions.

Experimental Group 1:2.5 mM ligatable nick, 20 g/L (B9-B12 total); Experimental Group 2:5 mM ligatable nick, 40 g/L; Experimental Group 3:10 mM ligatable nick, 80 g/L; and Experimental Group 4:15 mM ligatable nick, 120 g/L.

The concentrations of ATP in the reaction system were consistent with those of the ligatable nicks.

Experimental Groups 1~4 were respectively provided with a control group, and the inorganic pyrophosphatase was not added in the control group.

2. Synthesis of Nucleotide Strands and Analysis of Results

The synthesis of the nucleotide strands and analysis of the results were substantially the same as those in Example 1. Reaction products after 2 h, 16 h and 24 h of reaction were taken and tested, with results listed below.

TABLE 8

Conversion Rates of Products in Experimental Groups and Control Groups after 2 h, 16 h and 24 h in Example 4

| Variable | Reaction solution concentration | 2 h after Reaction AS Rate (%) Conversion | 2 h after Reaction SS Rate (%) Conversion | 2 h after Reaction Conversion Rate (%) | 16 h after Reaction AS Conversion Rate (%) | 16 h after Reaction Conversion SS Rate (%) | 16 h after Reaction Conversion Rate (%) | 24 h after Reaction AS Conversion Rate (%) | 24 h after Reaction Conversion SS Rate (%) | 24 h after Reaction Conversion Rate (%) |
|---|---|---|---|---|---|---|---|---|---|---|
| Experimental Group | 20 g/L | 44.23 | 43.17 | 87.4 | 53.12 | 43.16 | 96.3 | 52.91 | 43.28 | 96.19 |
| | 40 g/L | 29.01 | 42.72 | 71.73 | 52.28 | 42.99 | 95.3 | 52.24 | 42.92 | 94.98 |
| | 80 g/L | 0.57 | 23.26 | 23.83 | 50.47 | 41.28 | 91.8 | 51.96 | 41.57 | 93.53 |
| | 120 g/L | 0.28 | 16 | 16.28 | 11.7 | 41.65 | 53.4 | 28.03 | 42.01 | 70.04 |

TABLE 8-continued

Conversion Rates of Products in Experimental Groups and Control Groups after 2 h, 16 h and 24 h in Example 4

| Variable | Reaction solution concentration | 2 h after Reaction AS Rate (%) Conversion | SS Rate (%) Conversion | Conversion Rate (%) | 16 h after Reaction AS Conversion Rate (%) | Conversion SS Rate (%) | Conversion Rate (%) | 24 h after Reaction AS Conversion Rate (%) | Conversion SS Rate (%) | Conversion Rate (%) |
|---|---|---|---|---|---|---|---|---|---|---|
| Control Group | 20 g/L | 38.31 | 42.94 | 81.25 | 52.69 | 42.54 | 95.2 | 53.27 | 42.96 | 96.23 |
| | 40 g/L | 3.65 | 31.74 | 35.39 | 22.04 | 42.88 | 64.92 | 28.28 | 42.87 | 71.15 |
| | 80 g/L | 0.52 | 10.8 | 11.32 | 4.53 | 37.06 | 41.59 | 7.51 | 41.29 | 48.8 |
| | 120 g/L | 0.24 | 8.42 | 8.66 | 0.76 | 28.14 | 28.9 | 1.33 | 29.59 | 30.92 |

As can be seen from the results of the experimental groups, at the same enzyme amount, all of 20 g/L-80 g/L can achieve the conversion rates of approximately 90%. While for the control groups, the reaction concentrations 20 g/L exhibited the product conversion rates of approximately 95%, and 40 g/L-120 g/L showed significantly reduced conversion rates, particularly for the conversation rates of the AS strand product, which were lower than those of the experimental groups. Therefore, the present example demonstrates that for a high substrate concentration, for example, the ligatable nick concentration exceeding 2.5 mM, the reaction solution only containing RNA ligase exhibits slow reaction rates and low conversion rates, particularly when only a certain nick or some nicks complete the reaction prematurely, while others fail, adding the inorganic pyrophosphatase to the reaction system can enhance the reaction rate and conversion rate of the high-concentration substrates, especially when two nicks are present in the reaction, the inorganic pyrophosphatase has a notable advantage in accelerating the reaction rate of the subsequent nick.

The above-mentioned are merely for preferred embodiments of the present disclosure, but are not intended to limit the present disclosure. For those skilled in the art, various modifications and changes could be made to the present disclosure. Any amendments, equivalent replacements, improvements and so on, made within the spirit and principle of the present disclosure, should be covered within the scope of protection of the present disclosure.

What is claimed is:

1. A method for synthesizing a nucleotide strand, comprising: performing synthesis using an enzymatic ligation reagent, wherein the enzymatic ligation reagent comprises inorganic pyrophosphatase and nucleic acid ligase, wherein the inorganic pyrophosphatase and the nucleic acid ligase coexist in a reaction solution;
   - the nucleic acid ligase comprises a double-stranded ligase;
   - a substrate for the synthesis of the nucleotide strand is a nicked double-stranded nucleic acid molecule and/or a nucleic acid substrate capable of forming the nicked double-stranded nucleic acid molecule; and
   - optionally, conditions of the synthesis comprise: a temperature of 15-55° C. and a duration of 1-48 h.

2. The method for synthesizing the nucleotide strand according to claim 1, wherein
   - the double-stranded ligase optionally comprises a ligase ligating RNA duplexes and/or RNA/DNA hybrid duplexes;
   - optionally, the double-stranded ligases comprise any one or more of Rnl2 family ligases and Rnl5 family ligases; and
   - optionally, the Rnl2 family ligases comprise T4 RNA ligase 2.

3. The method for synthesizing the nucleotide strand according to claim 2, wherein the enzymatic ligation reagent further comprises any one or more of a buffer, ATP and divalent ions;
   - optionally, the divalent ions comprise any one or more of $Mg^{2+}$, $Mn^{2+}$, $Co^{2+}$ and $Zn^{2+}$; and
   - optionally, the buffer comprises any one of acetate buffer, phosphate buffer, Tris buffer and HEPES buffer.

4. The method for synthesizing the nucleotide strand according to claim 2,
   - wherein the nicked double-stranded nucleic acid molecule comprises: any one or more of nicked RNA duplexes and/or nicked RNA/DNA hybrid duplexes;
   - optionally, the nicked RNA/DNA hybrid duplexes comprise: a hybrid duplex composed of a DNA single strand and an RNA single strand via complementary base pairing and/or a hybrid duplex composed of a DNA/RNA hybrid single strand and a DNA or RNA single strand via complementary base pairing;
   - optionally, the nicked double-stranded nucleic acid molecule comprises nucleic acid substrates, or is formed by mixing the nucleic acid substrates, or mixing and then annealing the nucleic acid substrates;
   - optionally, the nucleic acid substrates are annealed at a temperature ranging from 0° C. to 100° C.;
   - optionally, the nucleic acid substrate comprises: any one or more of natural or modified RNA single strands, natural or modified RNA duplexes, natural or modified DNA single strands, natural or modified RNA/DNA hybrid single strands and natural or modified RNA/DNA hybrid duplexes;
   - optionally, in the nucleic acid substrate, the RNA single strands comprise linear RNA single strands and/or circular RNA single strands, the DNA single strands comprise linear DNA single strands and/or circular DNA single strands, the DNA single strands comprise linear DNA single strands and/or circular DNA single strands, the RNA/DNA hybrid single strands comprise linear RNA/DNA hybrid single strands and/or circular RNA/DNA hybrid single strands, and the RNA/DNA hybrid duplexes comprise linear RNA/DNA hybrid duplexes and/or circular RNA/DNA hybrid duplexes;

optionally, the RNA comprises: any one or more of mRNA, antisense oligonucleotides, siRNA, sgRNA, lncRNA, CircRNA and miRNA;

optionally, the nucleic acid substrate has a fragment length of ≥2 nt;

optionally, the nucleic acid substrate has the fragment length of 2-200 nt;

optionally, the number of nucleic acid substrates is ≥1;

optionally, a final concentration of the nucleic acid substrate is 0.01-100 mM; and optionally, the final concentration of the nucleic acid substrate is 1-100 mM.

* * * * *